(12) United States Patent  
Bacher et al.

(10) Patent No.: US 6,669,696 B2  
(45) Date of Patent: Dec. 30, 2003

(54) BIPOLAR MEDICAL INSTRUMENT

(75) Inventors: Uwe Bacher, Tuttlingen (DE); Martin Blocher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 10/084,562

(22) Filed: Feb. 26, 2002

(65) Prior Publication Data

US 2002/0128649 A1 Sep. 12, 2002

Related U.S. Application Data

(63) Continuation of application No. PCT/EP00/08072, filed on Aug. 18, 2000.

(30) Foreign Application Priority Data

Aug. 27, 1999 (DE) .......................................... 199 40 689

(51) Int. Cl.$^7$ ................................................ A61B 18/18
(52) U.S. Cl. .......................... 606/51; 606/206; 606/48
(58) Field of Search .................... 606/45, 46, 48–52, 606/206

(56) References Cited

U.S. PATENT DOCUMENTS

| 5,293,878 A | | 3/1994 | Bales et al. ................. 128/751 |
| 5,295,990 A | | 3/1994 | Levin .......................... 606/49 |
| 5,352,223 A | * | 10/1994 | McBrayer et al. ............. 606/51 |
| 5,396,900 A | * | 3/1995 | Slater et al. ................. 600/564 |
| 5,456,684 A | * | 10/1995 | Schmidt et al. ............... 606/41 |
| 5,743,906 A | | 4/1998 | Parins et al. ................. 606/51 |
| 5,827,281 A | * | 10/1998 | Levin .......................... 606/51 |
| 6,174,309 B1 | * | 1/2001 | Wrublewski et al. ......... 606/45 |
| 6,334,860 B1 | * | 1/2002 | Dorn ........................... 606/48 |
| 6,500,176 B1 | * | 12/2002 | Truckai et al. ............... 606/51 |

FOREIGN PATENT DOCUMENTS

| DE | 4312284 | * | 11/1993 |
| DE | 44 16 499 | | 11/1995 |
| DE | 296 04 191 | | 6/1996 |
| DE | 196 08 716 | | 4/1997 |
| DE | 199 40 689 | | 4/2001 |
| EP | 0 878 168 | | 11/1998 |
| WO | WO 99/40861 | | 8/1999 |

* cited by examiner

*Primary Examiner*—Michael Peffley  
(74) *Attorney, Agent, or Firm*—St. Onge Steward Johnston Reens LLC

(57) ABSTRACT

A bipolar medical instrument comprises a tubular shaft and two jaw parts. The jaw parts are arranged movably, one relative to the other, at the distal end of the tubular shaft and coupled one with the other via a joint. Each of the jaw parts forms a work electrode of different polarity. Each jaw part has associated to it a separate current line, one of such current lines being constituted by an axially movable force transmission element that is arranged in the tubular shaft and that is frictionally coupled to at least one of the jaw parts. At least one of the jaw parts comprises, at least in the region of the joint, a single-piece main body made from an electrically insulating material on which an electrically conductive jaw part insert is fastened, which forms a respective work electrode and which is connected, in an electrically conductive fashion, to the respective associated current line.

22 Claims, 6 Drawing Sheets

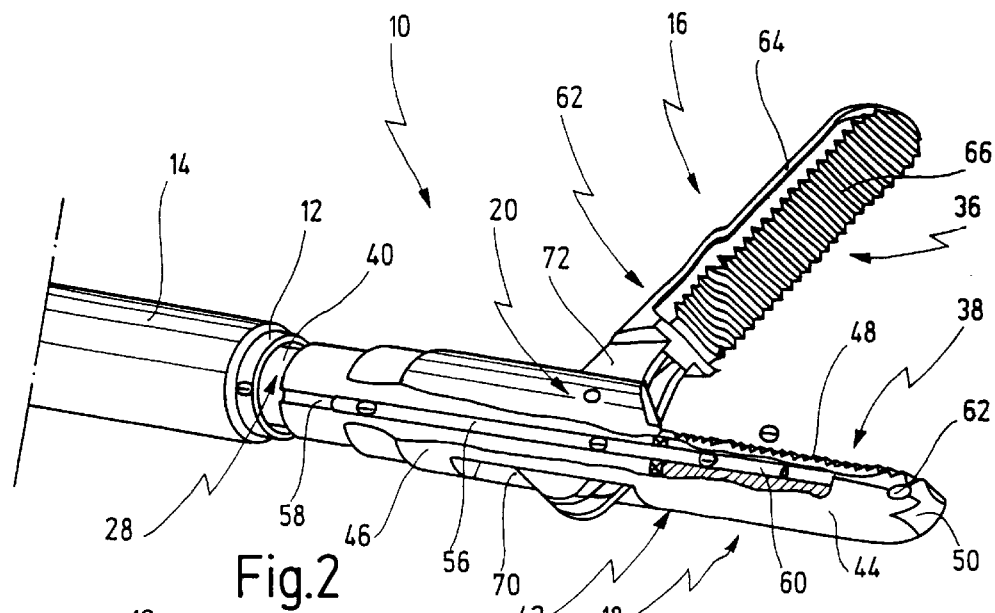
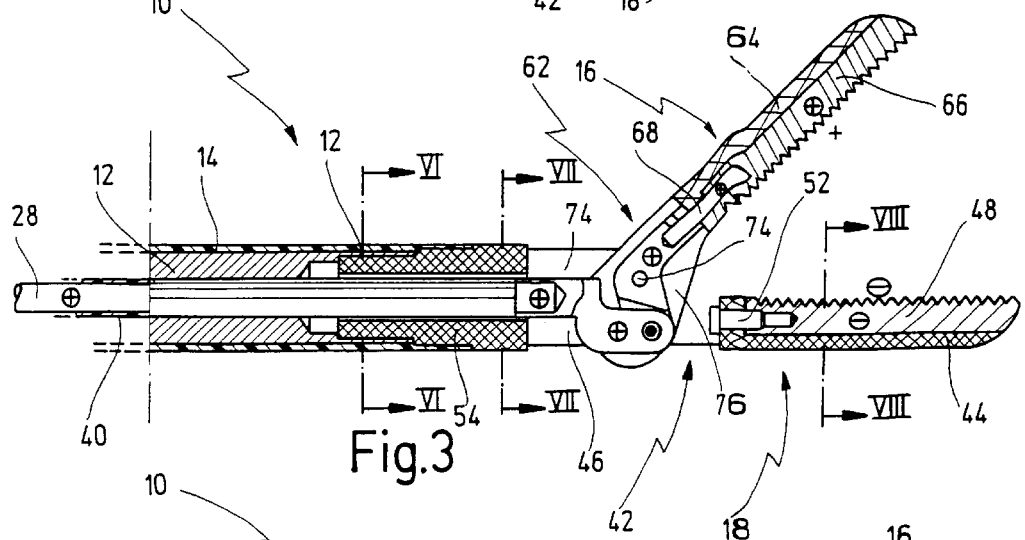
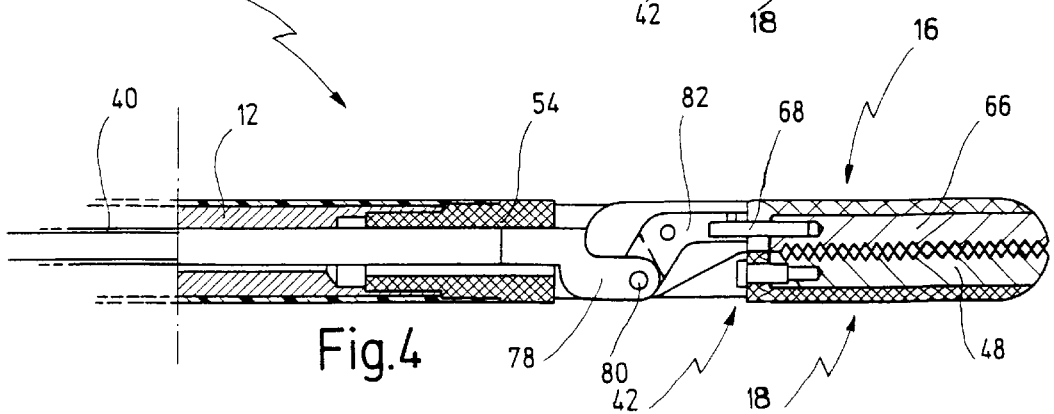

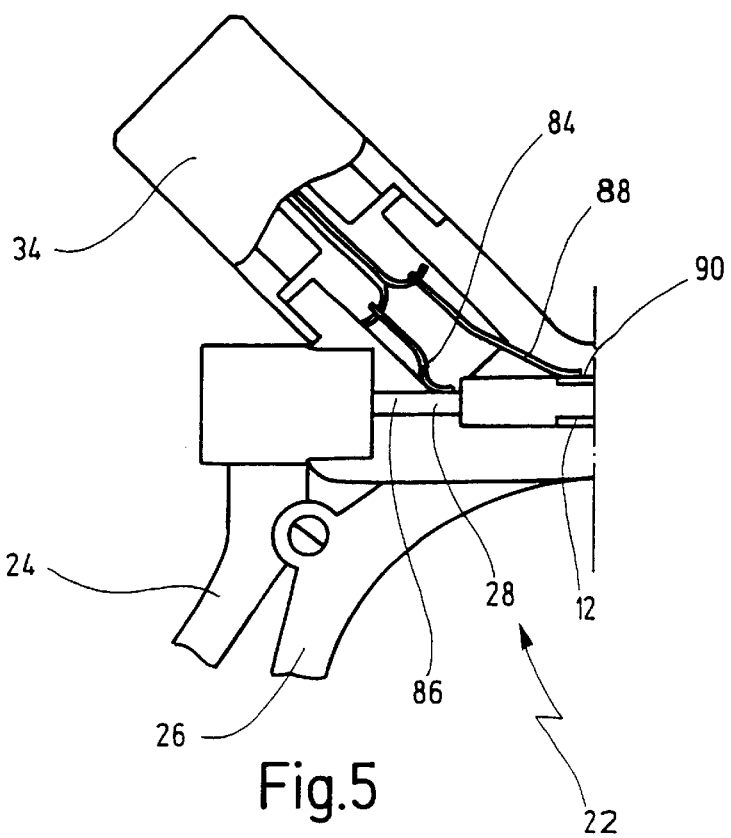
Fig.5
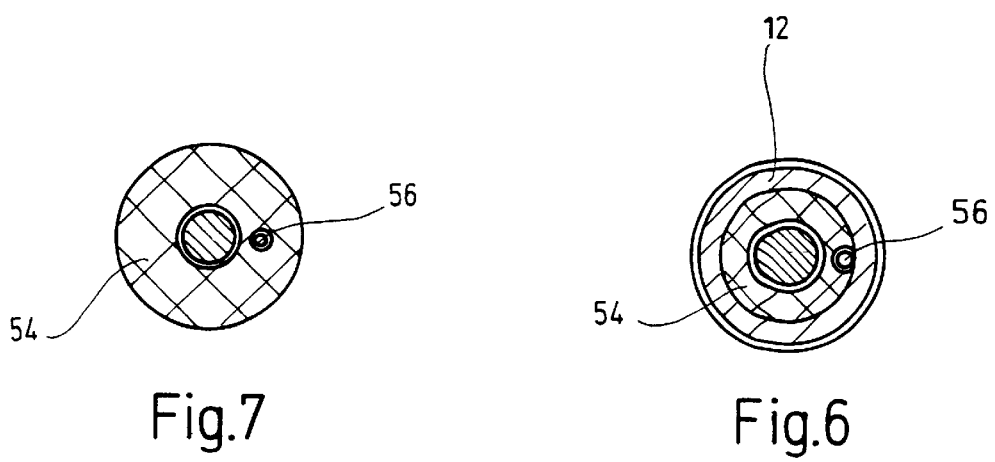
Fig.7
Fig.6

BIPOLAR MEDICAL INSTRUMENT

CROSS REFERENCE TO PENDING APPLICATION

This is a continuation of pending International Application PCT/EP00/08072 filed on Aug. 18, 2000 which designates the United States and which claims priority of German patent application 199 40 689.8 filed on Aug. 27, 1999.

BACKGROUND OF THE INVENTION

The present invention relates to a bipolar medical instrument comprising a tubular shaft with at least two jaw parts, which are arranged movably, one relative to the other, at the distal end of the tubular shaft and which are coupled via a joint, and each of which forms a work electrode of different polarity, with a separate current conductor being associated to each jaw part, one of such current conductors being constituted by an axially movable force transmission element that is arranged in the tubular shaft and is force-lockingly coupled to at least one of the jaw parts.

An instrument of this kind is known from DE 196 08 716 C1.

In minimally invasive surgery, an instrument of the before-mentioned kind is used for performing endoscopic operations in human or animal bodies.

The two jaw parts at the distal end of the tubular shaft are connected one with the other via a joint so that they can be opened and closed by actuation of a handle provided on the proximal end of the tubular shaft. Depending on the surgical application of such an instrument, the jaw parts are configured as cutting tools with cutting edges for cutting off tissue in the body, or as grasping tools and then with flatly abutting surfaces for grasping any cut-off tissue with the jaw parts in order to remove it from the body, or for holding an organ or a vessel so as to move it out of the operation field. Moreover, the jaw parts may have a combination of functions, namely a cutting and a grasping function.

At least one of the two jaw parts is connected with the tubular shaft in articulated fashion, while the other jaw part is connected with the tubular shaft either rigidly, or likewise in articulated fashion.

The before-mentioned kind of a medical instrument further provides that the two jaw parts each form a work electrode of different polarity that can be supplied with high-frequency (HF) current. Accordingly, each of the two jaw parts can be separately connected to one pole of a HF voltage source. By supplying the two jaw parts with a bipolar HF current it is possible, on the one hand, to increase the cutting effect by the thermal effect of the HF current in the tissue, if the tools are configured as cutting tools, while on the other hand, if they are configured as grasping tools, any tissue grasped between the jaw parts can be coagulated, and haemorrhages can be stopped, by the heat developed.

It is always a problem with such bipolar instruments to achieve a sufficient electric insulation effect between the two jaw parts in the region of the joint where the two jaw parts are in contact one with the other also in the open condition. When supplying the jaw parts with HF current, they must be electrically isolated as the two jaw parts are connected to different potentials. The problem of isolating the two jaw parts electrically is the greater the smaller such an instrument is configured in the region of the jaw parts and, thus, in the region of the joint. Small overall widths of the instrument in the area of the jaw parts are, however, especially important in minimally invasive surgery.

In the case of the instrument known from the before-mentioned DE 196 08 716 C1, the two jaw parts consist completely of metal and are, therefore, electrically conductive over their entire body. A force transmission element in the form of a push-and-pull rod is coupled with the two movable jaw parts via an articulated lever arrangement. The push-and-pull rod serves additionally as current conductor connecting one of the two jaw parts to the one pole of a HF voltage source.

In the case of this known instrument, the electric isolation of the two jaw parts is accomplished by ceramic elements which are inserted into the otherwise metallic joint of the two jaw parts and which, therefore, are themselves part of the joint. This way of electrically isolating the two jaw parts one from the other in the area of the joint provides, however, the disadvantage that when miniaturizing that instrument the size of the ceramic elements must be reduced as well. Since usually the HF frequency supplied to the jaw parts is in the range of 2.5 kV, this means that a voltage puncture may occur through the ceramic element in case that the size of the ceramic elements is reduced. Another disadvantage of the ceramic elements lies in the fact that the installed ceramic elements are subjected to frictional forces due to the movement of the jaw parts so that they may be crushed in the course of time. Further, it is a disadvantage of the configuration of the known instrument that the number of parts of the forceps in the region of the jaw parts and, thus, the constructional input and the cost of production of that known instrument, are undesirably increased.

From DE 43 12 284 A1 there has been further known a bipolar medical instrument where the jaw parts are completely made from a plastic material and stripped sections of current conductors are embedded in such plastic material. The jaw parts are configured as cutting members, consisting of plastic material, and work electrodes are embedded in the plastic material of the jaw parts. It is a disadvantage of that configuration that the current supply to the jaw parts is realized through separate electric conductors that are run through the push-and-pull rod in insulated fashion. The push-and-pull rod as such, therefore, does not serve as a current conductor in the case of these forceps. Consequently, this instrument is also connected with the disadvantage that the number of parts required is increased by the additional current conductors. An additional disadvantage lies in the fact that the end portions of the current conductors, that extend into the plastic material of the jaw parts, are subjected to bending stresses every time the jaw parts are opened or closed, so that the end portions may break in the course of time whereby the current flow to the electrodes would be interrupted.

An instrument similar to the instrument described above is known from WO 99/40861. This known medical bipolar instrument comprises, at the distal end of the shaft, two jaw parts that are movable one relative to the other, with one jaw part being movable, while the other jaw part is immovable. The movable jaw part is biased by means of a spring into a position in which it is pivoted away from the immovable jaw part, i.e. in which it occupies its open position. The actuating mechanism for the movable jaw part consists of a tubular shaft enclosing the shaft, which can be displaced in axial direction and which, when displaced in the distal direction, comes to slide onto the outer surface of the movable jaw part, whereby the latter is pressed against the immovable jaw part. The movable jaw part is coupled in articulated fashion with the immovable jaw part via a pin joint. The two jaw parts are again completely made from a plastic material, with metallic electrodes fastened to the plastic material. The current supply to the electrodes is again realized by individual conductors connected to the electrodes. Accordingly, this instrument is again connected with the disadvantage that the number of parts required is increased as a result of the additional current conductors and that the current supply lines, implemented as wires, are subjected to bending stresses during opening and closing of the jaw parts.

It is, therefore, the object of the present invention to improve a bipolar medical instrument of the before-mentioned type so that safe insulation of the jaw parts in the region of their joint is achieved without an increase in the number of parts and with lower constructional input.

SUMMARY OF THE INVENTION

According to the invention, this object is achieved with a bipolar instrument, comprising a tubular shaft having a proximal end and a distal end;

at least two jaw parts arranged movably, one relative to the other, at said distal end of said tubular shaft and coupled one to the other via a joint, each of said at least two jaw parts forming a work electrode of different polarity;

a separate current line for each of said at least two jaw parts, one of such current lines being constituted by an axially movable force transmission element arranged in said tubular shaft and force-lockingly connected to at least one of said jaw parts, wherein at least one of said jaw parts comprises, at least in the region of said joint, a single-piece main body made from an electrically insulating material on which an electrically conductive jaw part insert is fastened, which forms said respective work electrode and which is connected, in an electrically conductive fashion, to said respective associated current line.

It is, thus, provided according to the invention to equip at least one of the jaw parts with an electrically insulating single-piece main body. Such an electrically insulating main body may consist, for example, of a hard plastic material so that the instrument will meet the high demands placed on it in terms of stability in the area of its jaw parts. By having the connecting joint between the first jaw part and the second jaw part now arranged in the area of the single-piece insulating main body, electric isolation of the two jaw parts one from the other is now accomplished without any additional components, such as ceramic elements. The main body, being made from an insulating material, may be made particularly solid so that the stability of that jaw part and the stability of the joint are as high as if the jaw parts were completely made from metal. This configuration is suited for instruments where both jaw parts are movable, and also for instruments where one jaw part only is movable. The pin of the joint, which connects the two jaw parts one with the other in articulated fashion, may even be made from metal in the configuration of the invention, since any current transfer to the other jaw part is safely prevented by the main body consisting of an insulating material.

If only one jaw part is made movable the at least one jaw part that comprises the main body made from an electrically insulating material may be the immovable jaw part, for example, whereas the other movable jaw part, which is frictionally coupled to the force transmission element, may consist of metal in its entirety without any current transfer occurring from that movable jaw part to the immovable jaw part through the joint. It is possible in this way to realize the desired current flow between the force transmission element and the movable jaw part, without any additional connection measures. While in the case of the instrument known from DE 196 08 716 C1 an insulating ceramic element is also required in the area where the push-and-pull rod is hinged on the articulated lever arrangement, the present invention can do without any such additional insulating element. All in all, an especially simple structure of the instrument, requiring only a small number of parts, is achieved by the invention.

The object underlying the present invention is thus perfectly achieved.

According to a preferred embodiment, the main body comprises a distal section in which the jaw part insert, being arranged in that section, is enclosed on its outside in insulated fashion.

It is an advantage of this configuration that the HF current will come to act only on tissue that gets into contact with the working surface of the jaw part insert, while any tissue not involved in the operation, that may get into contact with the outside of the jaw part in the operation area, will not be impaired by the HF current. This permits the treatment of tissue with HF current to be carried out in a much more selective way.

According to another preferred embodiment, the jaw part insert is connected with the main body in friction-locking and in positive fashion.

The combined force-locking and positive connection provides the advantage that the jaw part insert is safely anchored on the main body. "Force-locking and positive connection" is to be understood in this case as sort of an interlocking connection between the jaw part insert and the main body that prevents the jaw part insert from being lifted off the main body. Such a connection may be implemented, for example, in the form of a T-shaped groove in the main body and a complementary T-shaped key on the jaw part insert. A force-locking and positive connection provides the particular advantage of high mechanical durability, which cannot be achieved by a jaw part insert cast into or embedded in the main body, as provided by the prior art. In addition, such a connection is especially temperature-resistant as it does without any connection of substances, as would occur if the connection were realized by cementing.

From the manufacturing point of view it is especially preferred if the jaw part insert is fastened on the main body by a dovetail connection.

The jaw part insert may be additionally secured on its proximal end by means of a screw or a pin to prevent relative movement with respect to the main body.

According to a further preferred embodiment, one of the jaw parts is rigidly connected with the tubular shaft, and at least that jaw part comprises the main body consisting of an electrically insulating material.

As has been mentioned before, this provides the advantage that the movable jaw part may be completely made from metal, in which case the current transfer from the force transmission element to the movable jaw part can be accomplished in a very simple way, constructionally. Since the immovable jaw part is fastened on the tubular shaft and since, accordingly, its proximal section corresponds to the diameter of the tubular shaft, in terms of dimension, this feature provides the additional advantage that the immovable jaw part can be configured to comprise a main body made from an insulating material with especially high rigidity.

It is especially preferred if each of the two jaw parts comprises a main body made from an electrically insulating material, with an electrically conductive jaw part insert, forming the respective work electrode of the jaw part, arranged thereon.

This feature provides the particular advantage that both jaw parts are completely insulated on their outside, at least in their proximal area, so that the HF current is applied only to such tissue that gets into contact with the jaw part inserts.

According to a further preferred embodiment, the tubular shaft forms the other current line, and the latter is connected with the other jaw part in electrically conductive fashion, while being insulated from the force transmission element.

This feature, which is known as such, contributes still further toward simplifying the structure of the forceps according to the invention, because no additional conductors are necessary for the current supply to the two jaw parts.

According to a further preferred embodiment, the main body made from insulating material is provided at least in that jaw part which is connected with the force transmission element, in which case the force transmission element is hinged on a proximal section of the main body on which an electrically conductive connection element is provided which then connects the force transmission element with the respective jaw part insert in electrically conductive fashion.

This embodiment, according to which the movable jaw part comprises a main body made from an electrically insulating material, is likewise advantageous. For, the proximal section of the main body made from an insulating material is bridged by the electrically conductive connection element, for the purpose of transferring the current to the jaw part insert, without the electrically conductive connection element being subjected to bending stresses during movement of the jaw part; this is so because an articulated, rather than a flexible, connection exists between the force transmission element and the connection element.

It is preferred in this connection if a pivot pin of the joint connecting the first jaw part with the second jaw part passes through the connection element.

The advantage of this arrangement lies in the fact that the connection element strengthens the pivot pin and prevents the pivot pin from working itself free in the non-metallic proximal section of the two jaw parts. The pivot pin of the joint may be electrically insulated, for example by a corresponding jacket, in order to ensure, in case the two ends of the pivot pin are exposed, that the entire outside of the instrument is insulated in the region of the joint of the jaw parts.

According to a further preferred embodiment, the force transmission element is connected to a current supply via a spring-loaded contact in a proximal region of the force transmission element.

Current transmission by means of a spring-loaded contact provides the advantage of a constructionally especially simple power supply to the axially movable force transmission element, which offers the additional advantage that the power supply as such can be stationarily arranged on the instrument itself, for example in the form of a connector housing or a connector socket for a cable.

According to certain preferred further developments of that feature, the spring-loaded contact is a wiper contact, for example an elongated metallic element in the form of a leaf spring, and/or the contact comprises an element, especially a ball, which is spring-loaded toward the force transmission element. This latter configuration provides the additional advantage that considerably less friction occurs between the ball and the force transmission element.

According to another preferred embodiment, the jaw part insert of the immovable jaw part, being connected with the tubular shaft, is connected in electrically conductive fashion with the tubular shaft via an electrically conductive wire element which is embedded in the proximal section of the second main body.

By having the element embedded in the main body of the immovable jaw part, this feature leads, advantageously, to an electrically conductive connection between the tubular shaft and the jaw part insert of the immovable jaw part, which is insulated from the force transmission element. Given the fact that the jaw part is immovable, the wire element is not subjected to bending stresses. In addition, the wire element, being embedded in the main body of the immovable jaw part, is protected from mechanical influences.

According to a further preferred embodiment, a proximal section of the second jaw part comprises a recessed portion with two legs extending in longitudinal direction, with the main body of the first jaw part being arranged between such legs and being connected with the legs in articulated fashion.

This feature provides the advantage that an especially slim, space-saving structure and a case-like connection between the two jaw parts is achieved.

According to a further preferred embodiment, a proximal section of the first jaw part comprises a fork section which is engaged by the force transmission element.

This feature provides the additional advantage that hinging the force transmission element on the movable jaw part can be accomplished in an especially sturdy and little space-consuming way.

According to a further preferred embodiment, the main body of the one jaw part and/or the main body of the second jaw part, if necessary, consist of a hard, especially a temperature-resistant plastic material.

This feature permits especially high stability of the main bodies of the jaw parts to be achieved. If in addition the plastic material is selected to be temperature-resistant, this provides the advantage that the jaw parts can be sterilized in an autoclave. Such hard plastic materials are generally known and available.

The forceps according to the invention can be configured as a grasping instrument, by giving mutually opposite inner surfaces of the work electrodes a planar surface, or as a cutting instrument, by configuring the mutually opposite inner faces of the work electrodes as cutting elements. The configurations according to the invention described above can be used with advantage for both types of instruments. When the work electrodes are configured as grasping tools, it is further preferred to give them complementary V-shaped cross-sections, whereby the tissue to be grasped is prevented from escaping laterally.

In cases where the work electrodes are configured as cutting elements, it is preferred if the inner surface of the one work electrode is provided with a notch extending in longitudinal direction, and the inner surface of the other work electrode is provided with a cutting edge coacting with that notch in cutting fashion.

This embodiment of the jaw parts is similar to that of anvil pliers which permit high cutting forces to be transferred to the tissue to be cut.

Other advantages will become apparent from the description that follows, and from the attached drawing.

It is understood that the features recited above and those yet to be explained below can be used not only in the respective combination indicated, but also in other combinations or in isolation, without leaving the context of the present invention.

BRIEF DESCRIPTION OF THE DRAWINGS

Exemplary embodiments of the invention are shown in the drawings and are explained in more detail in the description which follows. In the drawings:

FIG. 2 shows a perspective view of the forceps according to FIG. 1, in the region of the jaw part, in greatly enlarged scale;

FIG. 3 shows a longitudinal section through the forceps in the region of the jaw parts, with the jaw parts in their open position;

FIG. 4 shows a representation similar to that of FIG. 3, in which the jaw parts are in their closed position;

FIG. 5 shows a very diagrammatic, partially exposed representation of the proximal end of the forceps;

FIG. 6 shows a section along line VI—VI in FIG. 3;

FIG. 7 shows a section along line VII—VII in FIG. 3;

DETAILED DESCRIPTION OF PREFERRED EMBODIMENTS

Figure 1:
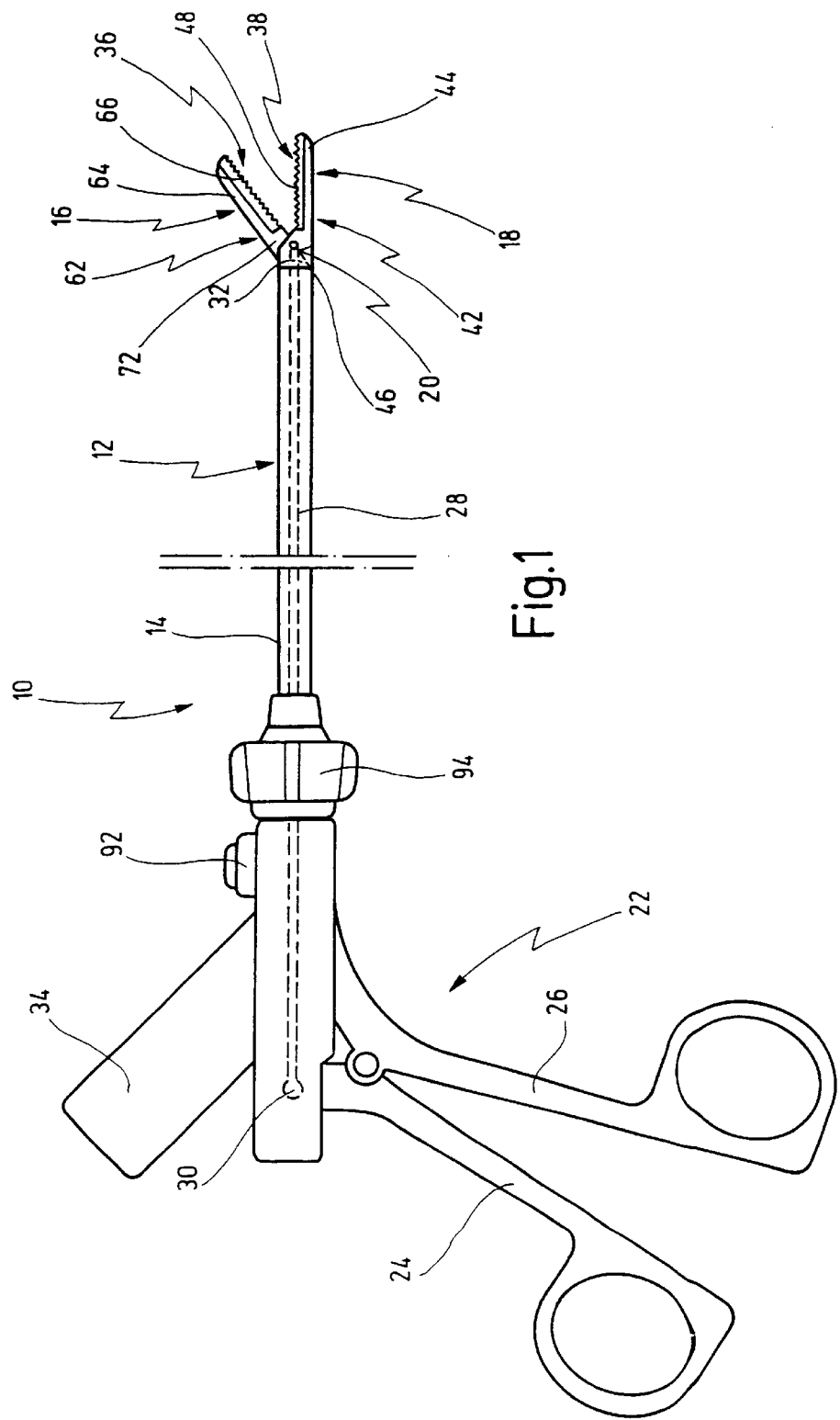
FIG. 1 shows an overall side view of a pair of bipolar medical forceps according to the invention.

FIG. 1 shows a bipolar medical instrument indicated in its entirety by the general reference numeral 10. Details of instrument 10 are apparent from FIGS. 2 to 9.

The instrument 10 is used in minimally invasive surgery for treating tissue in human or animal bodies, for preparation by means of HF current.

In the illustrated embodiment, the instrument 10 represents a grasping instrument, or a pair of grasping forceps, as will be described hereafter in more detail.

The instrument 10 has an elongated tubular shaft 12. The tubular shaft 12 is a metallic tube, configured as a current conductor, which is surrounded by an insulating enclosure 14.

The distal end of the tubular shaft 12 carries a first jaw part 16. Further, a second jaw part 18 is arranged on the distal end of the tubular shaft 12.

The first jaw part 16 and the second jaw part 18 are movable one relative to the other. In the illustrated embodiment, the first jaw part 16 is coupled movably with the tubular shaft 12, while the second jaw part 18 is coupled immovably with the tubular shaft 12.

The first jaw part 16 and the second jaw part 18 are joined in articulated fashion by a joint 20.

The instrument 10 is further provided, on its proximal end, with a handle 22 comprising a first movable handle element 24 and a second immovable handle element 26.

In order to move the first movable jaw part 16 relative to the second immovable jaw part 18, a force transmission element 28, configured in this case as a push-and-pull rod, extends between the movable handle element 24 and the immovable handle element 26. The force transmission element 28 is arranged for axial movement in the tubular shaft 12.

The force transmission element 28 has its proximal end 30 force-lockingly coupled with the movable handle element 24, for example via a ball/ball cup connection. The proximal end 32 of the force transmission element 28 is force-lockingly coupled with the movable jaw part 16, as will be described in more detail further below.

The proximal end of the instrument 10 further carries an obliquely projecting connector socket 34 through which the instrument 10 can be connected to an external HF voltage source not shown in the drawing.

The two jaw parts 16 and 18 each form a work electrode 36, 38 of different polarity, which means that in operation the work electrode 36 is connected to the one pole of the HF voltage source, whereas the work electrode 38 is connected to the other pole of the HF voltage source.

The force transmission element 28 also serves as a current line and is, therefore, configured as a metal part. Opposite the metallic tubular shaft 12, the force transmission element 28 is insulated by an insulating enclosure 40 applied on the force transmission element 28.

The force transmission element 28 serves as electrically conductive connection to the first jaw part 16, while the tubular shaft 12 serves as electric connection to the second jaw part 18, as will be described in more detail below.

Referring now to FIGS. 2 to 4 and 6 to 9, the region of the distal end of the instrument 10 will be described in more detail. The second jaw part 18 comprises a main body 42 formed integrally from an insulating material. The material may, for example, consist of a hard temperature-resistant plastic material with high bending strength.

The main body 42 comprises a distal section 44 and a proximal section 46.

The distal end 44 of the main body 42 carries a jaw part insert 48 which is electrically conductive and, preferably, made from metal. The jaw part insert 48 constitutes the work electrode 38.

Figure 8:
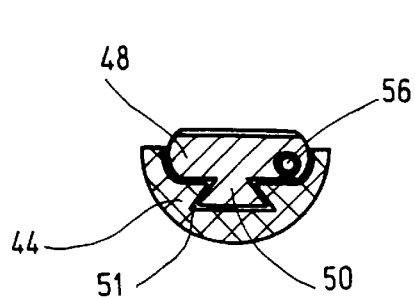
FIG. 8 shows a section along line VIII—VIII in FIG. 3.

As appears from FIGS. 2 and 8, the distal section 44 of the main body 42 covers the outside of the jaw part insert 48, which is enclosed therein, in insulating fashion so that any current transfer to tissue, that may get into contact with the outer surface of the main body 42 opposite the jaw part insert 48, is excluded.

The jaw part insert 48 is provided with a dovetail-shaped strip or key 50, by which the jaw part insert 48 engages a groove 51 of complementary shape in the main body 42 whereby a force-locking and positive connection, similar to an interlocking, is achieved with the main body 42. The dovetail-shaped key 50 is also electrically conductive, i.e. made from metal, and extends up to the distal tip of the jaw part 18 where it is not insulated from the outside.

At its proximal end, the jaw part insert 48 is connected with the main body 42 by screwing, by means of a bolt 52, so that it is secured on the main body 42 also against relative displacement with respect to the main body 42.

The proximal section 46 of the main body 42 is fastened in the tubular shaft 12 via a plug-in sleeve 54, which is formed integrally with the main body and which in addition consists of the same electrically insulating material, the connection being realized by a press fit and being secured, if necessary, by an adhesive.

The tubular shaft 12 is connected, in electrically conductive fashion, to the tubular shaft insert 48 of the second jaw part 18 via an electrically conductive wire element 56. As can be seen in FIGS. 2, 6 and 7, the wire element 56 is embedded in the main body 42 laterally from the longitudinal center axis of the main body 42, for which purpose a bore is provided that extends in the main body 42 and that ends in an open groove on its proximal end 58.

While FIG. 2 shows the main body 42 in its condition pulled off the shaft, it is evident that in the assembled condition the wire element 56 is pressed against the inner face of the tubular shaft 12 so as to establish intimate contact with the latter, whereby the current transfer from the tubular shaft 12 to the wire element 56 is guaranteed.

A distal end 60 of the wire element 56 projects into the jaw part insert 48 (compare FIG. 8) so that the current transfer from the wire element 56 to the jaw part insert 48 is guaranteed.

The before-mentioned bore extends also through the jaw part insert 48 and ends at the distal end in an opening 62. The opening 62 serves to facilitate the introduction of the wire element 56 into the jaw part insert 48 and the main body 42, and is sealed subsequently with an electrically insulating filling compound, for example an adhesive. The distal end 60 of the wire element 56 is located approximately midway in the jaw part insert 48.

The first jaw part 16 likewise comprises a main body 62 formed integrally from an electrically insulating material. The main body 62 has a distal section 64, again with an electrically conductive jaw part insert 66, constituting the work electrode 36, arranged in that section. The distal section 64 of the main body 62 and the jaw part insert 66 correspond to the distal section 44 of the main body 42 and the jaw part insert 48, respectively, so that these elements need not be described in more detail at this point.

The only difference lies in the fact that the jaw part insert 66 has its proximal end fixed on the main body 62 additionally by a pin 68.

The proximal section 46 of the main body 42 of the jaw part 18 exhibits, between the plug-in sleeve 54 and the distal end 44, a recessed portion 70 which accommodates a proximal section 72 of the main body 62 of the first jaw part 16. The recessed portion 70 is approximately rectangular in shape and forms two legs 74, of which the left leg is visible in FIGS. 3 and 4. The legs 74 form an integral connection between the plug-in sleeve 54 and the distal section 44 of the main body 42 and consist, accordingly, likewise of the same electrically conductive material.

The joint 20, which has been mentioned before with reference to FIG. 1 and which connects the movable jaw part 16 with the immovable jaw part 18 in articulated fashion, is now arranged on the proximal section 72 of the main body 62 and the proximal section 46 of the main body 42, i.e. proximally behind the jaw part inserts 48 and 66, respectively.

The joint 20 is constituted by a pivot pin 74 that passes the legs 74 of the main body 42 and the proximal section 72 of the main body 62. The pivot pin 74 is electrically insulated at least at those ends that are exposed on the main body 42.

The proximal section 72 of the main body 62 of the first jaw part 16 is shaped as a fork section 76 which is engaged by the force transmission element 28.

The force transmission element 28 is provided for this purpose, at its distal end, with a hinge section 78 formed as an angle. As can be seen in FIG. 3, the hinge section 78 is attached to the distal end of the force transmission element 28, although it would well be imaginable to make it an integral part of the remaining body of the force transmission element 28. The hinge section 78 of the force transmission element 28 is not insulated on its outside, but may be provided with an insulating coating although this is not necessary in the present case. The hinge section 78 is force-lockingly coupled with the proximal section of the main body 62 via a pivot pin 80, the latter being electrically conductive and free from any insulating enclosure.

In order to transfer the current supplied by the force transmission element 28 to the jaw part insert 66, an electrically conductive connection element 82 is arranged between the hinge section 78 and the jaw part insert 66, which connection element 82 is firmly connected with the fork section 76 of the main body 62, but coupled in articulated fashion with the force transmission element 28. The electrically conductive connection between the connection element 82 and the jaw part insert 66 is finally effected by the electrically conductive pin 68.

The current flow between the tubular shaft 12 and the jaw part insert 48 of the second jaw part 18 is realized by the wire element 56. This current flow is indicated in FIG. 2 by minus signs.

The current flow between the force transmission element 28 and the jaw part insert 66 is realized via the hinge section 78, the connection element 82, the pin 68. This current flow is indicated in FIG. 3 by plus signs. In addition, the pivot pin 80 takes part in realizing that current flow.

The jaw part inserts 66 and 48 form work electrodes 36 and 38, whose effective working surfaces are formed by flat abutting faces so that the work electrodes 36 and 38 are designed as grasping tools, which means that the instrument 10 can be used as grasping forceps. In order to improve the grip of the work electrodes 36 and 38, the abutting working surfaces of the jaw part inserts 66 and 48 have a serrated configuration, as can be seen especially well in FIG. 2.

Figure 10:
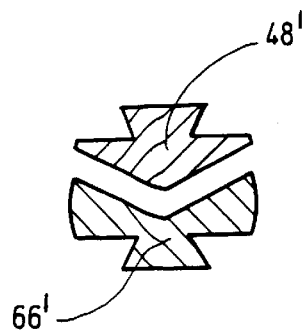
FIG. 10 shows a cross-section through another example of the configuration of the jaw part inserts.
Figure 9:
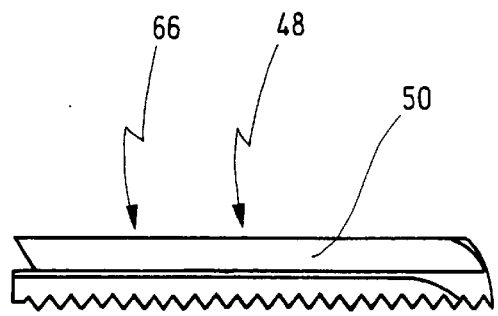
FIG. 9 shows a side view of the jaw part insert according to FIG. 8, without the respective main body.

FIG. 10 shows a modified embodiment, compared with the jaw part inserts 48 and 66, where the jaw part inserts 48' and 66', illustrated in FIG. 10 without their respective main bodies, are provided with working surfaces that exhibit complementary cross-sectional V-shapes.

Figure 11:
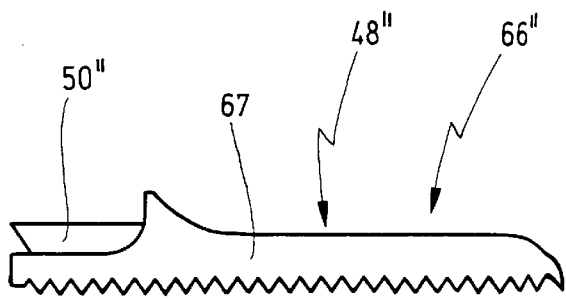
FIG. 11 shows a side view of still another example of a jaw part insert.
Figure 12:
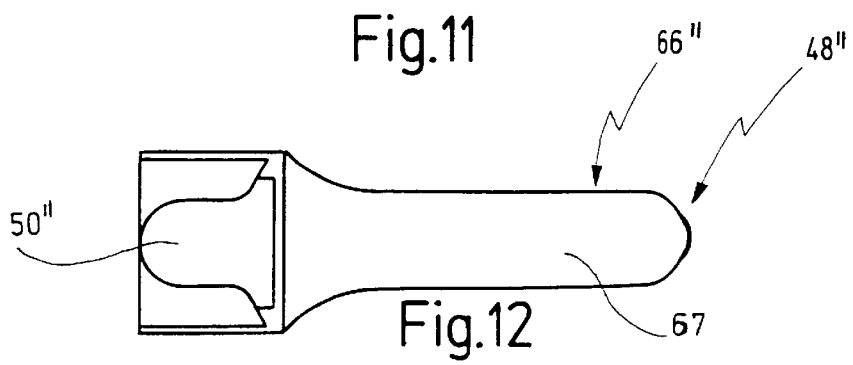
FIG. 12 shows a top view of the jaw part insert according to FIG. 11.

FIGS. 11 and 12 show another example of a possible embodiment of jaw part inserts 4" and 66", respectively, suited especially for particularly slim jaw parts.

With this configuration of the jaw part inserts 48" and 6", the latter are provided with the dovetail-shaped key 50" only on their proximal ends so that the jaw part inserts 48" and 66" are coupled force-lockingly and positively with the corresponding main body, not shown in FIGS. 11 and 12, only at their proximal ends, while their distal section 67 is not enclosed by the main body. Thus, the distal section 67 of the jaw part inserts 48" and 66" is not insulated on the outside in the case of this embodiment.

Figure 13:
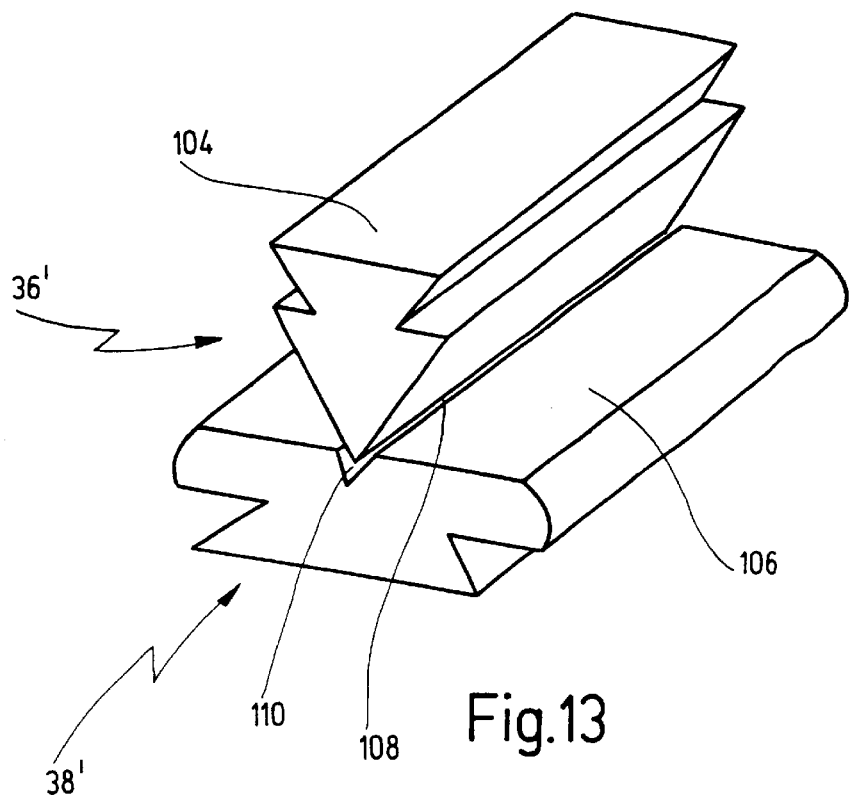
FIG. 13 shows a perspective view of still another example of the configuration of the jaw part inserts.

FIG. 13 shows another example of jaw part inserts 104 and 106 for use in connection with the instrument 10. The jaw part inserts 104 and 106 form work electrodes 36' and 38', respectively, formed as cutting tools. To this end, the jaw part insert 104 is provided with a cutting edge 108 that coacts with a notch 110 in cutting fashion.

Figure 14:
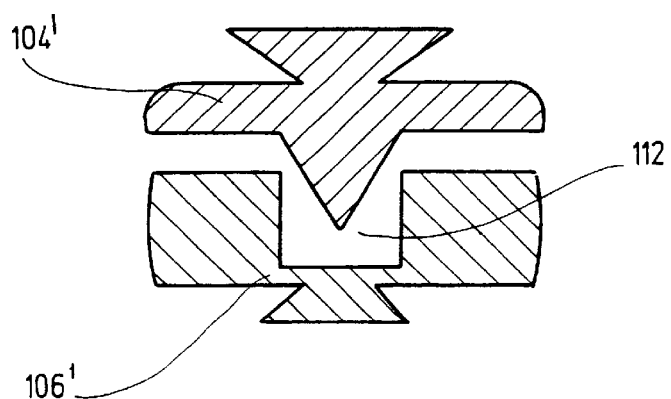
FIG. 14 shows a cross-section through still another example of jaw part inserts.

While the notch 110, as shown in FIG. 13, has a substantially V-shaped cross-section, FIG. 14 shows an embodiment where a notch 112 of a jaw part insert 106' has a rectangular cross-section. A jaw part insert 104' coacting with the jaw part insert 106' is modified with respect to the jaw part insert 104 insofar as the jaw part insert 104' extends laterally over approximately the same width as the jaw part insert 106'. When the jaw parts, containing the jaw part inserts 104' and 106', are closed, the lateral areas of the jaw part inserts 104' and 106' come into planar contact one with the other.

With the jaw part inserts 104 and 106, or 104' and 106', respectively, shown in FIGS. 13 and 14, the instrument 10 can thus be used as a bipolar electric cutting instrument.

From FIG. 5 it is further apparent that the current transfer from the contact pole of the connector 34, associated with the force transmission element 28, is effected via a spring-loaded contact designed as wiper contact 84 formed by a spring wire which is elastically biased toward a non-insulated section 86 of the force transmission element 28.

A second contact 88 presses upon a non-insulated proximal end 90 of the tubular shaft 12 in order to connect the tubular shaft 12 conductively with the other contact pole of the connector 34. It is, however, understood that the tubular shaft 12 is immovable so that the contact 88 is not a wiper contact.

Figure 15:
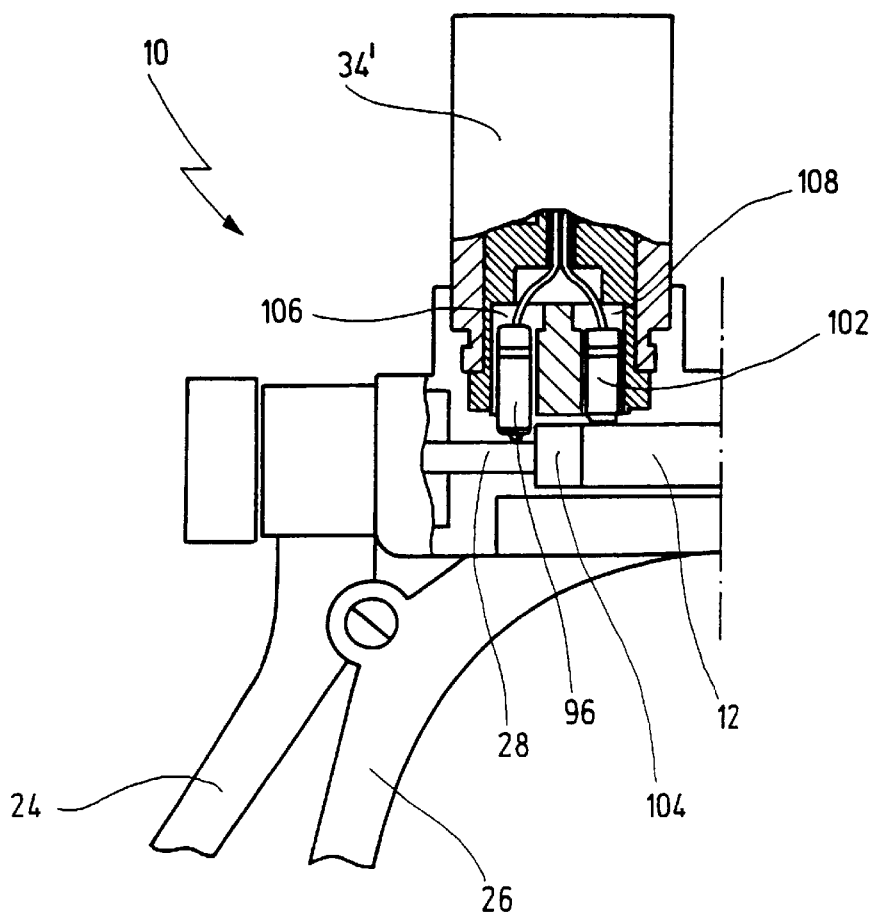
FIG. 15 shows a representation, corresponding to FIG. 5, of the proximal end of the forceps according to another embodiment.
Figure 16:
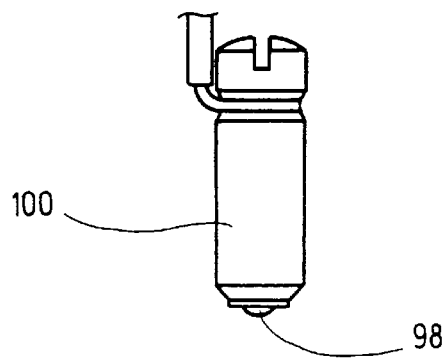
FIG. 16 shows a side view, rotated by 90°, of a detail from FIG. 15 in enlarged scale.

FIGS. 15 and 16 show another example of the proximal end of the instrument 10, modified with respect to FIG. 5, in which parts identical to or comparable with the embodiment of FIG. 5 are identified by the same reference numerals.

Contrary to the embodiment illustrated in FIG. 5 and in FIG. 1, a connector socket 34' is configured to extend approximately vertically relative to the instrument axis.

With this embodiment, the current transfer to the force transmission element 28 is effected by a spring-loaded contact 96, the contact between the corresponding supply line and the force transmission element 28 being realized by a spring-loaded ball 98 which is held in a housing 100 and is urged in downward direction against the force transmission element 28 by a spring—not shown—arranged in the housing 100.

Another spring-loaded contact 102, similar in construction to the contact 96, serves for transferring the current to the tubular shaft 12, and an insulating element 104 is arranged at the proximal end of the tubular shaft 12 as isolation between the force transmission element 28 and the tubular shaft 12.

The contacts 96, 102 are received in spaces 106 and 108 in the connector socket 34', where they are insulated one from the other.

Referring again to FIG. 1, the tubular shaft 12, together with the force transmission element 28 and the jaw parts 16 and 18, can be rotated about the longitudinal axis for which purpose there is provided a setting wheel 98, connected with the tubular shaft 12.

There is further provided a locking mechanism 92 by means of which the tubular shaft 12 and, thus, the force transmission element 28, are locked detachably on the handle 22.

What is claimed is:

1. A bipolar medical instrument, comprising:
   a tubular shaft having a proximal end and a distal end;
   at least two jaw parts arranged movably, one relative to the other, at said distal end of said tubular shaft and coupled one to the other via a joint, each of said at least two jaw parts forming a work electrode of different polarity;
   a separate current line for each of said at least two jaw parts, one of such current lines being constituted by an axially movable force transmission element arranged in said tubular shaft and forcelockingly connected to at least one of said jaw parts,
   wherein at least one of said jaw parts comprises, at least in the region of said joint, a single-piece main body made from an electrically insulating material on which an electrically conductive jaw part insert is fastened, which forms said respective work electrode and which is connected, in an electrically conductive fashion, to said current line for said jaw part; and
   wherein said jaw part insert is connected with said main body in force-locking and in positive fashion and is fastened on said main body by a dovetail connection.

2. The instrument of claim 1, wherein said main body comprises a distal section in which said jaw part insert is enclosed on its outside in insulated fashion.

3. The instrument of claim 1, wherein one of said jaw parts is immovably connected with said tubular shaft, and at least that jaw part comprises said main body consisting of an electrically insulating material.

4. The instrument of claim 1, wherein each of said two jaw parts comprises a main body made from an electrically insulating material, with said electrically conductive jaw part insert, forming said respective work electrode of said jaw parts, being fastened thereon.

5. The instrument of claim 1, wherein said tubular shaft forms the other current line, and the latter is connected with said other jaw part in electrically conductive fashion, while being insulated from said force transmission element.

6. The instrument of claim 1, where in said main body made from insulating material is provided at least in that jaw part which is connected with said force transmission element, in which case said force transmission element is hinged on a proximal section of said main body on which an electrically conductive connection element is provided which then connects said force transmission element with the respective jaw part insert in electrically conductive fashion.

7. The instrument of claim 6, wherein a pivot pin of said joint connecting said first jaw part with said second jaw part passes through said connection element.

8. The instrument of claim 1, wherein said force transmission element is connected to a current supply via a spring-loaded contact in a proximal region of said force transmission element.

9. The instrument of claim 8, wherein said spring-loaded contact is a wiper contact.

10. The instrument of claim 1, where in said force transmission element is connected to a current supply via a spring-loaded contact in a proximal region of said force transmission element, and wherein said contact comprises an element, which is spring-loaded toward said force transmission element.

11. The instrument of claim 3, wherein said jaw part insert of said jaw part, which is immovably connected with said tubular shaft, is connected in electrically conductive fashion with said tubular shaft via an electrically conductive wire element which is embedded in said main body of said jaw part.

12. The instrument of claim 1, wherein a proximal section of said second jaw part comprises a recessed portion with two legs extending in longitudinal direction, with a proximal section of said jaw part being arranged between such legs and being connected with said legs in articulated fashion.

13. The instrument of claim 1, wherein a proximal section of said first jaw part comprises a fork section which is engaged by said force transmission element.

14. The instrument of claim 1, wherein said main body of said one jaw part consists of a hard plastic material.

15. The instrument of claim 1, wherein mutually opposite inner surfaces of said work electrodes are given in planar surface, so that said work electrodes coact as grasping tools when said jaw parts are closed.

16. The instrument of claim 1, wherein mutually opposite inner surfaces of said work electrodes are configured as cutting elements, so that said work electrodes coact as cutting tools when said jaw parts are closed.

17. The instrument of claim 1, wherein mutually opposite inner surfaces of said work electrodes are configured as cutting elements, so that said work electrodes coact as cutting tools when said jaw parts are closed.

18. The instrument of claim 17, wherein said inner surface of said one work electrode is provided with a notch extending in longitudinal direction, and said inner surface of said other work electrode is provided with a cutting edge coacting with said notch in cutting fashion.

19. A bipolar medical instrument, comprising:

a tubular shaft having a proximal end and a distal end;

at least two jaw parts arranged movably, one relative to the other, at said distal end of said tubular shaft and coupled one to the other via a joint, each of said at least two jaw parts forming a work electrode of different polarity;

a separate current line for each of said at least two jaw parts, one of such current lines being constituted by an axially movable force transmission element arranged in said tubular shaft and forcelockingly connected to at least one of said jaw parts, wherein at least one of said jaw parts comprises, at least in the region of said joint, a single-piece main body made from an electrically insulating material on which an electrically conductive jaw part insert is fastened, which forms said respective work electrode and which is connected, in an electrically conductive fashion, to said current line for said jaw part; and wherein one of said jaw parts is immovably connected with said tubular shaft, and at least that jaw part comprises said main body having an electrically insulating material and is connected in electrically conductive fashion with said tubular shaft via an electrically conductive wire element which is embedded in said main body of said jaw part.

20. A bipolar medical instrument, comprising:

a tubular shaft having a proximal end and a distal end;

at least two jaw parts arranged movably, one relative to the other, at said distal end of said tubular shaft and coupled one to the other via a joint, each of said at least two jaw parts forming a work electrode of different polarity;

a separate current line for each of said at least two jaw parts, one of such current lines being constituted by an axially movable force transmission element arranged in said tubular shaft and forcelockingly connected to at least one of said jaw parts, wherein at least one of said jaw parts comprises, at least in the region of said joint, a single-piece main body made from an electrically insulating material on which an electrically conductive jaw part insert is fastened, which forms said respective work electrode and which is connected, in an electrically conductive fashion, to said current line for said jaw part; and wherein a proximal section of said second jaw part comprises a recessed portion with two legs extending in longitudinal direction, with a proximal section of said jaw part being arranged between such legs and being connected with said legs in articulated fashion.

21. A bipolar medical instrument, comprising:

a tubular shaft having a proximal end and a distal end;

at least two jaw parts arranged movably, one relative to the other, at said distal end of said tubular shaft and coupled one to the other via a joint, each of said at least two jaw parts forming a work electrode of different polarity;

a separate current line for each of said at least two jaw parts, one of such current lines being constituted by an axially movable force transmission element arranged in said tubular shaft and forcelockingly connected to at least one of said jaw parts, wherein at least one of said jaw parts comprises, at least in the region of said joint, a single-piece main body made from an electrically insulating material on which an electrically conductive jaw part insert is fastened, which forms said respective work electrode and which is connected, in an electrically conductive fashion, to said current line for said jaw part; and wherein a proximal section of said first jaw part comprises a fork section which is engaged by said force transmission element.

22. A bipolar medical instrument, comprising:

a tubular shaft having a proximal end and a distal end;

at least two jaw parts arranged movably, one relative to the other, at said distal end of said tubular shaft and coupled one to the other via a joint, each of said at least two jaw parts forming a work electrode of different polarity, with at least one of said jaw parts comprising a single-piece main body made from an electrically insulating material in which an electrically conductive jaw part insert is located that forms the respective work electrode for the respective jaw part;

a separate current line for each of said at least two jaw parts, one of such current lines being constituted by an axially movable force transmission element arranged in said tubular shaft and forcelockingly connected to at least one of said jaw parts and said electrically conductive jaw part insert located in the single-piece main body is electrically connected to the current line.

* * * * *